United States Patent [19]

Kitamura et al.

[11] 4,443,730
[45] Apr. 17, 1984

[54] BIOLOGICAL PIEZOELECTRIC TRANSDUCER DEVICE FOR THE LIVING BODY

[75] Inventors: Mitsuaki Kitamura; Toshio Nakayama; Kunio Kamimura, all of Kyoto; Iwao Seo; Tomonobu Yaguchi, both of Amimachi, all of Japan

[73] Assignee: Mitsubishi Petrochemical Co., Ltd., Tokyo, Japan

[21] Appl. No.: 377,388

[22] Filed: May 12, 1982

Related U.S. Application Data

[63] Continuation of Ser. No. 93,211, Nov. 13, 1979, abandoned.

[30] Foreign Application Priority Data

Nov. 15, 1978 [JP] Japan ................................. 53-14659

[51] Int. Cl.³ .......................................... H01L 41/08
[52] U.S. Cl. .................................. 310/330; 310/331; 310/358; 310/800
[58] Field of Search ................................ 310/330–332, 310/800, 323, 363–366, 324, 337, 340, 358

[56] References Cited

U.S. PATENT DOCUMENTS

| 2,095,376 | 10/1937 | Bechmann ............................ 310/364 |
| 3,333,236 | 7/1967 | Schloss ............................ 310/337 X |
| 3,622,815 | 11/1971 | Schafft ................................ 310/332 |
| 3,750,127 | 7/1973 | Ayers et al. ................... 310/800 X |
| 3,798,474 | 3/1974 | Cassand et al. ................ 310/800 X |
| 4,166,229 | 8/1979 | De Reggi ........................... 310/337 |

*Primary Examiner*—Mark O. Budd
*Attorney, Agent, or Firm*—Donald D. Mon; David O'Reilly

[57] ABSTRACT

A biological transducer device for measuring blood pressure, heart pulse, heart sound etc. comprising a high molecular piezoelectric element which is in a thin film or ribbon form so that the transducer is very pliable so as to make close accurate contact with a measuring point on a human body without producing any creases. The piezoelectric element is enclosed in netting comprised of a metal wire mesh so that the transducer is completely shielded from outer mechanical and electrical noise.

23 Claims, 11 Drawing Figures

BIOLOGICAL PIEZOELECTRIC TRANSDUCER DEVICE FOR THE LIVING BODY

CROSS REFERENCE TO OTHER APPLICATION

This is a continuation application of application Ser. No. 093,211, filed Nov. 13, 1979, now abandonded.

BACKGROUND OF THE INVENTION

The present invention relates to a biological transducer device having a thin film, high molecular piezoelectric element which provides excellent pliability for measuring blood pressure, pulse wave, pulse rate, intracardiac sound, and heart noise etc. The biological transducer is particularly suitable for contacting an artery of a living body for converting the vibration or sound of the living body into electrical signals.

The blood pressure is one of the many sources of information about a living body which can be obtained without entering a blood vessel. Heretofore, blood pressure is measured, in general, by the following method. A manschette or cuff is first wrapped around the arm of a human body and air is injected into the manschette by a hand operated air pump, to increase the pressure in the manschette until the sound or pulse in the artery beneath the manschette disappears. Then the pressure in the manschette is decreased slowly. The pressure in the manschette and the systolic blood pressure will be equal when a sound, called the Korotkov sound, synchronized with heart pulse, appears. The pressure in the manschette is also equal to diastolic blood pressure when this sound (i.e. Korotkov sound) disappears. However, in this prior method the Korotkov sound is detected by using a stethoscope in contact with the artery at a point near the manschette. The operator uses his judgement to determine by ear the pressure at the appearance or disappearance of the Korotkov sound so that great skill is needed for operation and detection of blood pressure and errors in judgement can easily occur.

Recently in the development of electronics, other detecting methods and means instead of the stethoscope method have been proposed and utilized. For example detecting devices employing direct transmitting means such as a strain gauge, a solid piezoelectric material (PZT, Rochelle salt etc.) or an air transmitting means such as micro-phone or optical means are proposed. However, these prior devices, including the stethoscope are only suitable for measuring at a particular spot and is necessary to skillfully and accurately contact the measuring point. Moreover, the mechanical impedance of the proposed transducer is larger than the mechanical impedance of the skin or cutis at the measuring point. Thus impedance matching is wrong so that these transducers hinder the movement in the artery, resulting in low detection sensitivity and poor reproduction (i.e. the same result can not be expected by repeating the measurement). Moreover, the transducer device employing a strain gauge or solid piezoelectric element is complicated in construction, sensitive to shock and can easily break.

BRIEF SUMMARY OF THE INVENTION

One object of the present invention is to eliminate the above drawbacks and provide a biological transducer device having great pliability to simplify attachment in close contact with the measuring point to provide improved reproduction.

Another object of the present invention is to provide a biological transducer device in which a film like high molecular piezoelectric element having great pliability is utilized so that the mechanical impedance of the piezoelectric element is small enough to permit detection of the movement in an artery and accurately convert the pulse in the artery into an electric signal.

Yet another object of the present invention is to provide a biological transducer device having a belt like configuration so that it may be easily wrapped around an extremity of the human body such as an arm providing excellent operation. With the transducer of the present invention it is possible to make close accurate contact with the measuring point of an artery for more reliable measurement and improved reproduction.

Still another object of the present invention is to provide a biological transducer device having a transducer in which an auxiliary electrode extends along an electrode layer of said piezoelectric element so it is possible to use the transducer to collect electric charges even if a part of the electrode mounted on the piezoelectric element is cut or broken.

Yet a further object of the present invention is to provide a biological transducer device in which a lead wire is connected to the piezoelectric element at a position near one end so as to keep other end of the element free.

Still a further object of the present invention is to provide a biological transducer device in which two piezoelectric elements are superimposed on each other to increase tensile strength, sensitivity due to the piezoelectric effect and signal to noise (S/N) ratio.

Yet another object of the present invention is to provide biological transducer device in which an auxilliary electrode is attached near one end of the piezoelectric element, with the other remaining part or end remaining free to allow free displacement between them to prevent breaking of each element due to repeated bending while keeping the assembly flexible or very pliable.

Still another object of the present invention is to provide biological transducer device in which a net like cover comprised of metal wire is provided around each element so as to completely shield them. The wires of the netting extend at 45 degrees to the longitudinal direction of said element to allow free bending of the element.

Other and further objects, features and advantages of the invention will become more apparent from the following description, when considered in conjunction with the accompanying drawings.

DETAILED DESCRIPTION OF THE INVENTION

Referring to the attached drawings, FIGS. 1 to 5 inclusive, there is shown the first embodiment of the present invention.

Figure 1:
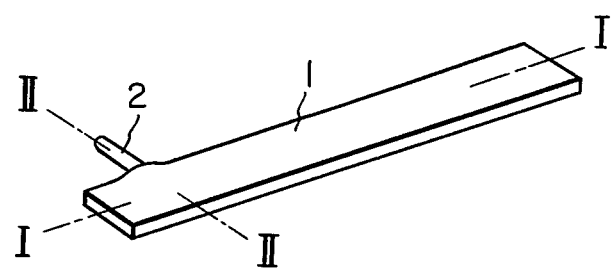
FIG. 1 is a perspective view of the first embodiment of the present invention.

In the drawings, numeral 1 designates a body having a piezoelectric element having excellent flexibility while 2 is a low noise shielded cable for transmitting an electric signal from the body 1. As shown in FIG. 1 the body is formed in a belt like configuration so as to wrap closely around the arm of a human body with minimum clearance to contact the point to be measured, such as an artery, accurately and easily. Moreover it is reliable in operation and provides improved reproduction.

Figure 2:
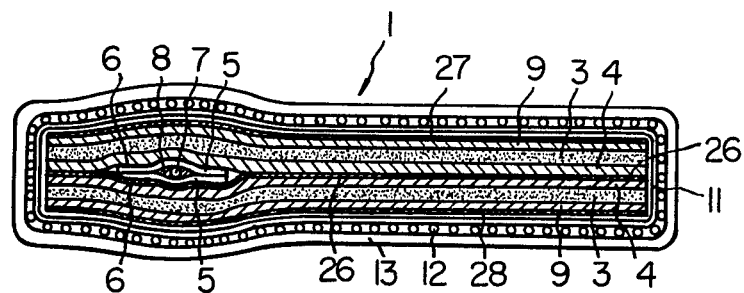
FIG. 2 is a cross-sectional view taken on line 1—1 of FIG. 1.

As shown in FIG. 2, there are two piezoelectric elements, 3 in the form of thin sheets or films of a high molecular piezoelectric material. Materials for said high molecular piezoelectric material comprise as follows:

A. Organic high molecular piezoelectric material:
   1. Natural high polymer such as cellulose of protein.
   2. Poly-γ-methyl-L-glutamate.
   3. A synthetic organic polymer such as; polyvinyl fluoride, polyvinylidene fluoride, polyvinyl chloride, polyacrylonitrile, polycarbonate and the like.

B. A composite mixture of a synthetic resin and piezoelectric ceramics; the mixture being of high dielectric ceramic 90% to 10% by volumn and synthetic resin 10% to 90% by volumn comprising:
   1. A ferroelectric ceramic: $BaTiO_3$, $PbTiO_3$-$PbZrO_3$.
   2. A synthetic resin such as: polyamide, polyvinylidene fluoride, polyacetal.

The powder of said ceramic is added to the matrix of said synthetic resin. The diameter or fineness of said ceramic powder is 0.2 to 44μ (microns) and is preferably 1 to 5μ for greatest piezoelectric effect and formation of the composite. Good results can be obtained by adding a polar, high molecular material such as an acrylo nitrile-butadiene rubber (NBR), a chlorinated polyethylene, a fluoric rubber or a epichlorohydrine rubber to high mechanical strength, a crystalline and polar high molecular material such as polyvinylidene fluoride, nylon, acetal resin etc.

The high molecular material and the ceramic powder are mixed and melted by an extruded, a roller or kneader, and formed into a film or sheet 0.01 to 1 mm thickness by press formation, extruder formation, calender formation or casting formation using a solvent.

The piezoelectric film or sheet is stretched, if necessary, and electrode layers are formed on both surfaces (i.e. opposite sides) by vacuum sputtering, plating with aluminum or smearing a conductive paste which is a mixture of metal powder such as silver and resin for forming a thin layer with a solvent. The film or sheet is heated from ambient or room temperature up to 170° C. and preferably 30° to 150° C. to provide piezoelectricity before or after formation of the electrode layers. A DC electric field or DC and AC electric field is applied to the film or sheet during the heated condition, from 0.5 to 6 hours on both surfaces (i.e. opposite sides) of the film or sheet which is then cooled rapidly or gradually so as to be electret.

For example, a ferroelectric ceramic powder substance (zirconate-lead titanate) was mixed with polyacetal resin under the component ration of 50/50% volume; the mixture was then formed into a film 100μ in thickness and an electrode layer was formed on both surfaces of the film. The film was poled under condition of 200 KV/cn at 60 C. The piezoelectric modulus $d_{31}$ is $28 \times 10^{-12}$ C/N (coulombs/newton) and Young's modulus E is $1.50 \times 10^9$ $NM/m^2$ (newtons/meter$^2$) of the film. The film produced has great flexibility so that it makes close contact with the human body, is not anisotropic so that there is no limitation on fixing its direction which simplifies manufacturing.

As shown in FIG. 2, the film of piezoelectric material is cut into a piece of 2-20 mm width and 30-250 mm length. A pair of piezoelectric elements thus obtained are superimposed on each other so their electrode layers 4, 4 provided on the anode faces of the elements 3, 3 are in contact. Electrodes 9, 9 are provided on the opposite face of the elements 3, 3. A pair of solid (i.e. continuous) electrode plates 5, 5 such as a phosphor bronze piece are interposed in part between said electrode layers 4, 4 and secured or bonded in place by suitable means such as a conductive adhesive 6, 6. A lead wire 7 from the cable 2 is inserted between the electrode plates 5, 5 from a lateral direction and secured by solder 8. The width of the electrode plates 5, 5 is equal to or slightly less than the width of the piezoelectric sheet elements 3, 3 and the length of the electrode plates 5, 5 is 5-20 mm and is preferably secured at a position near one end of the piezoelectric elements 3, 3. An auxiliary electrode 26 such as a thin film of aluminum, tin or a conductive resin having a width and length less than that of element 3 is interposed between said elements 3, 3. A part of the auxiliary electrode 26 near the electrode plate 5 is secured electrically to the piezoelectric element 3, 3 however, the remaining part or portion of the auxiliary electrode 26 is not secured to allow free displacement between the piezoelectric elements. The free displacement between the elements due to these unsecured ends protects each element from breaking due to repeated bending while in use. Even if part of electrode 4, 4 does break the auxiliary electrode 26 can collect electric charges produced near the ends of the broken element enabling full use.

As explained above, the superimposed construction of two piezoelectric elements 3, 3 without securing them firmly provides following advantages.

1. The electric charges due to the piezoelectric effect is increased and the sensitivity and signal to noise ratio is doubled.

Figure 4:
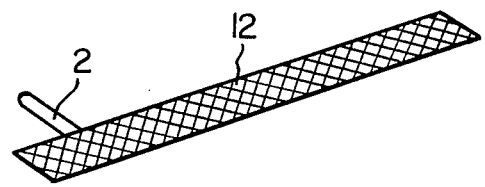
FIG. 4 is a perspective view of net-like cover.

2. The shielding effect from external noise is increased because the cathodes of the piezoelectric elements 3, 3 face outward Lead wires 10, 10 are connected to electrode layers 9, 9 provided at the cathode of said piezoelectric elements 3, 3, facing outward, and auxiliary electrodes 27, 28 are in contact with and secured to electrode layers 9, 9 in the vicinity of lead wires 10, 10. An insulating film 11 such as a polyethylene film is formed around the auxiliary electrodes 27, 28 and a netting or mesh 12 consisting of stainless steel wires, copper wires or brass wire as shown in FIG. 4 is wrapped around the protective film 11 at a bias to form a 45° angle between each wire of the netting or mesh 12 and the planar direction of the piezoelectric elements 3,3. The netting 12 consists of wire having diameter of less than 55μ and the spacing or distance between each wire is less than 88μ. An outer skin 13 consisting of a flexible plastic sheet is provided to cover the assembly or netting 12.

Figure 3:
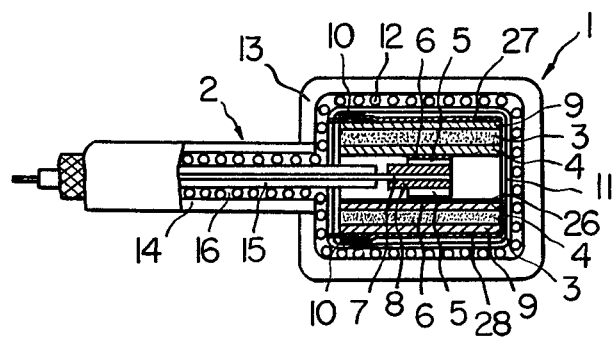
FIG. 3 is a cross-sectional view taken on line II—II of FIG. 1 together with part of the cable.

As shown in the embodiment of FIG. 3, a low noise cable 2 and a shield wire 16 is provided between the outer tube 14 and inner tube 15. The cable 2 also consists of an insulator, and the shield wire 16 is connected to the lead wire 10.

Figure 5:
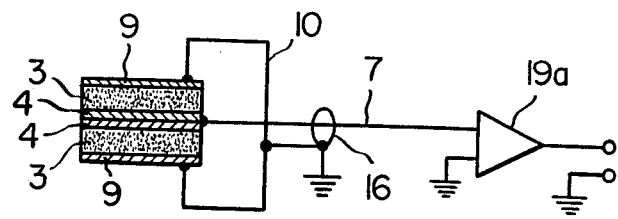
FIG. 5 is a electrical circuit diagram of the first embodiment of the invention.

FIG. 5 is an electrical circuit diagram of the device of FIGS. 1–4. The piezoelectric elements 3,3 are connected in parallel through electrode layers 4,4 and the output signal of the piezoelectric elements 3,3 is transmitted from electrode layers 4,4, 9,9 through lead wire 7 and shield wire 16 to an amplifier 19a.

Figure 6:
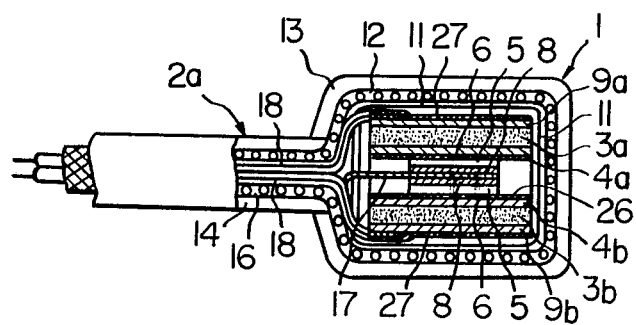
FIG. 6 is a cross-sectional view of a second embodiment of the invention corresponding to the view shown in FIG. 3.
Figure 7:
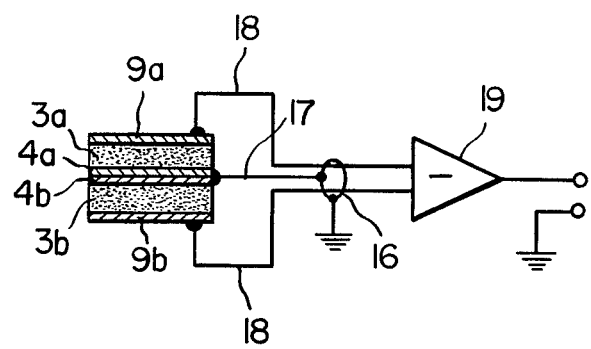
FIG. 7 is an electrical circuit diagram of the second embodiment of the invention.

FIGS. 6–7 illustrates a second embodiment of the present invention in which the cathode of the upper piezoelectric element 3 is superimosed toward the anode of the lower piezoelectric element 3 and their electrode layers 4a, 4b are in contact with electrodes plates 5,5 using conductive adhesive 6. A lead wire 17 is inserted between electrode plates 5,5 and secured by solder 8 thereto as before.

The elctrode layers 9a, 9b at the anode side of upper piezoelectric element 3 and the cathode side of lower piezoelectric element 3 respectively are connected to lead wires 18,18 in the two core shield cable 2a respectively.

As shown in FIG. 6, the shield wire 16 of the cable 2a is connected to the lead wire 17 and the netting 12.

Of course, three auxilliary electrodes 26, 27 and 27 are provided in the same manner as in the first embodiment.

FIG. 7 is an electrical circuit diagram of said second embodiment showing the piezoelectric elements 3,3 connected in series through electrodes 4a, 4a. The output signals of the piezoelectric elements 3,3 are transmitted from electrode layers 9a, 9b through lead wires 18, 18 to a differential amplifier 19.

In this device, the output signal from the upper piezoelectric element and lower piezoelectric element are picked up separately and transmitted to the differential amplifier, therefore the following advantages are obtained.

1. The voltage of the output signals is doubled.
2. The influence from temperature variations or external electrical noise is cancelled.

Figure 8:
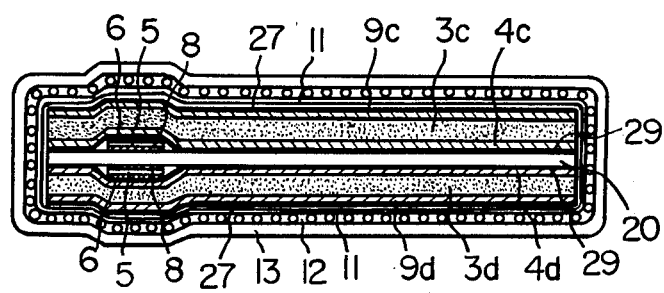
FIG. 8 is a cross-sectional view of a third embodiment of the invention corresponding to the sectional view of FIG. 2.
Figure 9:
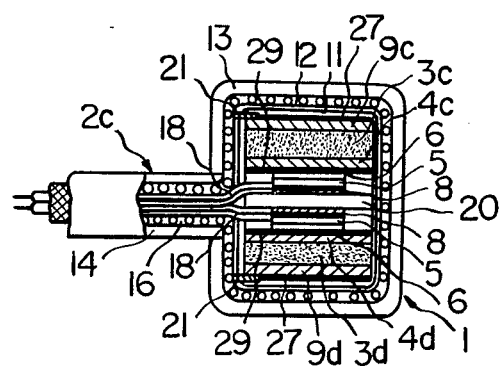
FIG. 9 is a cross-sectional view of the third embodiment of the invention corresponding to the view shown in FIG. 3.
Figure 10:
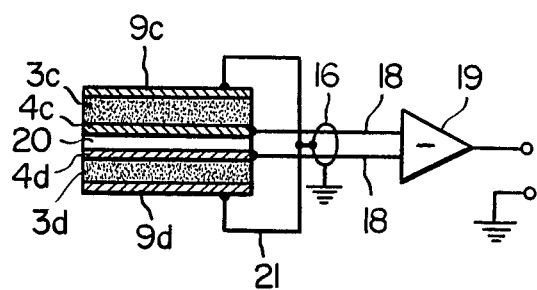
FIG. 10 is an electrical circuit diagram of the third embodiment of the invention.

FIGS. 8 to 10 illustrates a third embodiment of the present invention as shown in FIGS. 8 and 9, the electrode layer 4c at the lower cathode face of upper piezoelectric element 3c is in opposition to the electrode layer 4d at the upper anode face of lower piezoelectric element 3d with an insulating layer 20 between. The insulating layer 20 is a film of 1–50μ thickness such as polyethlene, polyester, polystyline, insulating paper, rubber etc. These electrode layers 4c, 4d are connected to lead wires 18,18 of cable 2c respectively. These outer electrode layers 9c, 9d are connected to lead wires 21, 21 which in turn are connected to netting 12 and shield wire 16 of said cable 2c. Auxiliary electrodes 29, 29 are provided at both surfaces of the insulating layer 20 as before. Electrodes 27, 27 are also auxiliary electrodes extending along the outer electrodes 9c, 9d of element 3c, 3d.

FIG. 10 is an electrical circuit diagram of the third embodiment showing the piezoelectric elements 3c, 3d connected in series through electrode layers 9c, 9d and lead wire 21 with an insulating layer 20 between the elements. The output signals of these piezoelectric elements 3c, 3d are transmitted from electrode layers 4c, 4d through lead wires 18, 18 to the differential amplifier 19.

This third embodiment has improved shielding effect over the construction shown in the second embodiment.

Figure 11:
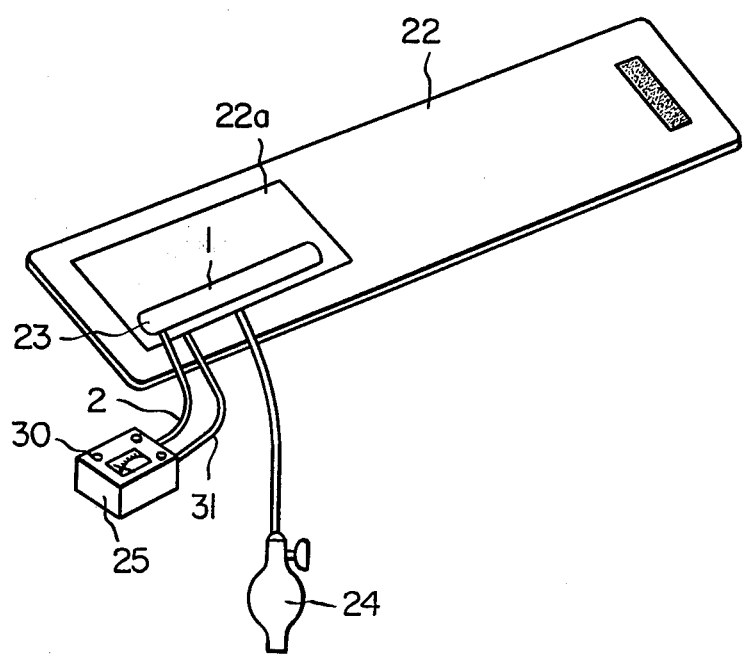
FIG. 11 is an perspective view illustrating the operation of the present invention with a blood pressure meter.

FIG. 11 illustrates the operation of the biological transducer device of the present invention with a sphygmomanometer or blood pressure meter.

As shown in FIG. 11, the body 1 connected to the cable 2 is attached to and in contact with an air bag 22a of a cuff 22 having an elongated belt like shape for fastening to a human body. The top of body 1 having the cable 2 is connected to the air bag 22a at the secured portion 23 near one end of the body 1. The other unsecured end of the body 1 is left free. A pump 24 is provided for supplying air to said bag 22a. Device 25 has a meter for measuring air pressure in the air bag 22a by a strain gauge method introduced through tube 31 and an amplifier (not shown in FIG. 11) which is connected to cable 2 of body 1, the amplifier 19 triggers an alarm device 30, such as a lamp provided on the upper face of the device 25 when the piezoelectric elements 3, 3, on the body 1 detect a Korotkov sound in an artery.

The operation of above device is as follows:

In use, the cuff 22 with body 1 is wrapped around the arm. Then air bag 22a is expanded by pump 24 for clamping the arm until the flow of blood in the artery is stopped. Air in bag 22a is then released gradually and the pressure in bag 22a slowly decreases. When the pressure in bag 22a is equal to the systolic blood pressure the Korotkov sound generates a response in the transducer body 1 which detects the Korotkov sound illuminating the alarm device 30 while the device 25 indicated the systolic pressure on the meter.

The pressure in bag 22a continues to decrease further until the pressure in bag 22a is equal to the diastolic blood pressure at which time the Korotkov sound ceases. The transducer body 1 detects it and the alarm device indicates it while the meter on device 25 measures the diastolic blood pressure.

In said device, the body having the piezoelectric element is secured to the cuff only at one end while the other end of the body is free and extends along the cuff. Therefore the transducer device may uniformly conform to and contact the human body without producing any crease and the biological transducer device may contact the measuring point, such as an artery of a human body accurately in an extended state and detects the blood pressure of a human body precisely without producing errors and converts the pressure into an electric signal. Moreover, the piezoelectric element is enclosed in netting consisting of conductive wire so that the transducer is completely shielded from external mechanical or electrical noise.

While in the device shown in FIG. 11, only one biological transducer device is provided on the cuff, it is possible to provide more than one biological transducer and connect them in parallel for covering an accident to prevent mistouching a human body with one of them.

The utility of the biological transducer device is not limited to measuring blood pressure only but may be used to detect any vibrations or sounds in a human body, such as pulse rate, pulse wave intracardiac sound, pulsation of viens, breath, and may be used with a sphygmomanometer.

What is claimed is:

1. A biological transducer device comprising a flexible organic film like high molecular peizoelectric element having electrode layers secured to both surfaces of opposite sides; a lead wire connected to each of said electrode layers; thin film auxiliary electrodes connected to said lead wires extending along the electrode layers of said piezoelectric element, at least one of said auxiliary electrodes being secured to one electrode layer at one end with the other end being free to allow free to allow free displacement of said one auxiliary electrode; an insulating film formed around the piezoelectric element; shielding mens for shielding the piezoelectric element; and a protective skin covering the exterior of said shielding means whereby the assembly is flexible.

2. A biological transducer device as claimed in claim 1, in which said piezoelectric element is a thin film and each lead wire is connected at a position near one end of said piezoelectric element.

3. A biological transducer device as claimed in claim 1, in which the piezoelectric element is a flexible thin film in the range of 2-20 mm width, 30-250 mm length and 0.01-1 mm thickness.

4. A biological transducer device as claimed in claim 1, in which said shielding means is a netting consisting of wire having a diameter of less than 55 spaced at a distance of less than 88, each wire extending at an angle of 45 degrees to the longitudinal direction of said piezoelectric element.

5. A biological transducer device as claimed in claim 1, in which said piezoelectric element comprises a pair of piezoelectric elements superimposed on each other, a lead wire positioned between said piezoelectric elements at a position near one end, the lead wire and piezoelectric elements being secured at said one end so that the other end of the piezoelectric elements are free so as to allow free displacement, The upper and lower faces of said superimosed pair of piezoelectric elements being connected electrically.

6. A biological transducer device as claimed in claim 5, includes an electrode plate between said piezoelectric elements; said lead wire being connected to the electrode plate.

7. A biological transducer device as claimed in claim 5, including auxiliary electrodes provided above, below and between said piezoelectric elements; said auxiliary electrodes being secured to each other at a position where said lead wires are connected.

8. A biological transducer device as claimed in claim 6, wherein said electrode plate is a continuous plate.

9. A biological transducer device as claimed in claim 1, in which said piezoelectric element is a flexible thin film consisting of a synthetic resin in the range of 10 to 90% by volume, and a ferroelectirc ceramic in the range of 90 to 10% volume.

10. A biological transducer as claimed in claim 9, in which said synthetic resin is a polyacetal resin.

11. A biological transducer device comprising; a pair of flexible film like high molecular piezoelectric elements, electrode layers secured to opposite sides of each of said piezoelectric elements, said piezoelectric elements being superimposed on each other, a thin film auxiliary electrode interposed between said piezoelectric elements; further thin film auxiliary electrodes extending along the electrode layers at the upper and lower faces of said superimposed piezoelectric elements, an electrode plate interposed between said piezoelectric elements; a lead wire connected to said electrode plate at a position near one end of said piezoelectric elements, said interposed auxiliary electrode being secured to the adjacent electrode layers and said electrode plate at a position where said lead wire is connected; said further auxiliary electrodes being connected at one end to the adjacent electrode layers to allow free displacement of said auxiliary electrodes; an insulating film surrounding said piezoelectric elements and electrodes; shielding means for shielding the piezoelectric elements; and a flexible protective skin covering the exterior of said shielding means.

12. A biological transducer device comprising;
a thin film piezoelectric element;
electrode means secured to the respective surfaces of said piezoelectric element;
a thin film auxiliary electrode extending along each electrode means secured to the surfaces of said piezoelectric element;
t least one lead wire connected to each of said electrodes of said piezoelectric element;
said auxiliary electrodes being secured to said electrode means at one end with the other ends being free to allow free displacement of said auxiliary electrodes;
an insulating film surrounding said piezoelectric element and electrodes;
shield means substantially surrounding said piezoelectric element;
a flexible protective skin covering the exterior of said shield means;
said piezoelectric elements being comprised of high molecular piezoelectric material.

13. The biological transducer device according to claim 12, wherein said high molecular material is an organic material.

14. The biological transducer device according to claim 13, wherein said organic material is a natural high polymer from the group consisting of cellulose or protein.

15. The biological transducer device according to claim 13, wherein said organic material is poly-γ-methyl-L-glutamate.

16. The biological transducer device according to claim 13, wherein said organic material is a synthetic organic polymer from the group consisting of polyvinyl fluoride, polyvinylidene fluoride, polyvinyl chloride, polyacrylonitrile or polycarbonate.

17. The biological transducer device according to claim 12, wherein said high molecular material is a composite mixture of a synthetic resin and a piezoelectric ceramic.

18. The biological transducer device according to claim 17, wherein said composite mixture is comprised of a ratio of 10 to 90% by volume of a synthetic resin mixed with 90 to 10% by volume of a piezoelectric ceramic.

19. The biological transducer device according to claim 18, wherein said piezoelectric ceramic is a ferroelectric ceramic.

20. The biological transducer device according to claim 19, wherein said ferroelectric ceramic is from the group consisting of $BatiO_3$, or $PbTiO_3$-$PbZrO_3$.

21. The biological transducer device according to claim 18, wherein said synthetic resin is from the group consisting of polyamide, polyvinylidene fluoride, or polyacetal resin.

22. The biological transducer device according to clim 18, wherein said ceramic is a ceramic powder having a fineness in the range of 0.2 to 44 microns.

23. The biological transducer device according to claim 22, wherein said ceramic powder has a fineness between 1 to 5 microns.

* * * * *